(12) United States Patent
Kawabata et al.

(10) Patent No.: US 10,151,727 B2
(45) Date of Patent: Dec. 11, 2018

(54) AUTOMATIC LOCALIZED SUBSTRATE ANALYSIS DEVICE AND ANALYSIS METHOD

(71) Applicants: IAS Inc., Tokyo (JP); Shin-Etsu Handotai Co., Ltd., Tokyo (JP)

(72) Inventors: Katsuhiko Kawabata, Tokyo (JP); Tatsuya Ichinose, Tokyo (JP); Toshihiko Imai, Fukushima (JP)

(73) Assignees: IAS, INC., Tokyo (JP); SHIN_ETSU HANDOTAI CO., LTD., Tokyo (JP)

( * ) Notice: Subject to any disclaimer, the term of this patent is extended or adjusted under 35 U.S.C. 154(b) by 0 days.

(21) Appl. No.: 15/322,389

(22) PCT Filed: Jul. 21, 2015

(86) PCT No.: PCT/JP2015/070681
§ 371 (c)(1),
(2) Date: Dec. 27, 2016

(87) PCT Pub. No.: WO2016/027607
PCT Pub. Date: Feb. 25, 2016

(65) Prior Publication Data
US 2017/0160233 A1    Jun. 8, 2017

(30) Foreign Application Priority Data
Aug. 20, 2014    (JP) .................................. 2014-167171

(51) Int. Cl.
*G01N 27/62* (2006.01)
*G01N 1/28* (2006.01)
(Continued)

(52) U.S. Cl.
CPC .............. *G01N 27/62* (2013.01); *B01L 3/021* (2013.01); *B01L 3/0262* (2013.01);
(Continued)

(58) Field of Classification Search
CPC ......... G01N 1/02; G01N 1/10; H01J 49/0031; H01J 49/0027; H01J 49/0404; H01J 49/04;
(Continued)

(56) References Cited

U.S. PATENT DOCUMENTS

| | | |
|---|---|---|
| 5,783,938 A | 7/1998 | Munson et al. |
| 2001/0023130 A1 | 9/2001 | Gilton et al. |

(Continued)

FOREIGN PATENT DOCUMENTS

| | | |
|---|---|---|
| JP | 5-256749 A1 | 10/1993 |
| JP | 5-283498 A1 | 10/1993 |

(Continued)

OTHER PUBLICATIONS

Supplementary European Search Report, EP 15833717.0, dated Mar. 23, 2018.

(Continued)

*Primary Examiner* — Christopher Adam Hixson
(74) *Attorney, Agent, or Firm* — Roberts & Roberts, LLP

(57) ABSTRACT

An object of the present invention is to provide an analysis apparatus in which local analysis of a substrate with ICP-MS is automated. The present invention relates to an automatic analysis apparatus for a local region of a substrate, including: a nozzle for local analysis having: analysis-liquid supply means that ejects analysis liquid onto a substrate; analysis-liquid discharge means that takes the analysis liquid including an object to be analyzed from the substrate into the nozzle to feed the analysis liquid to a nebulizer; and exhaust means including an exhaust channel in the nozzle; automatic liquid-feed means that automatically feeds the collected analysis liquid to ICP-MS; flow adjustment means that adjusts the flow of the analysis liquid; and automatic control means that simultaneously performs local analysis and (Continued)

analysis of the object to be analyzed with the ICP-MS to perform automatic analysis to a plurality of adjacent predetermined regions, successively.

2 Claims, 3 Drawing Sheets

(51) Int. Cl.
*G01N 35/10* (2006.01)
*G01N 1/00* (2006.01)
*B01L 3/02* (2006.01)
*G01N 1/32* (2006.01)
*H01J 49/04* (2006.01)
*H01J 49/10* (2006.01)

(52) U.S. Cl.
CPC .............. *B01L 3/0293* (2013.01); *G01N 1/00* (2013.01); *G01N 1/28* (2013.01); *G01N 1/32* (2013.01); *G01N 35/10* (2013.01); *G01N 35/1002* (2013.01); *G01N 35/1016* (2013.01); *G01N 35/1095* (2013.01); *B01L 2200/0684* (2013.01); *B01L 2200/082* (2013.01); *H01J 49/045* (2013.01); *H01J 49/105* (2013.01)

(58) Field of Classification Search
CPC ............... H01J 49/0431; H01J 49/0459; H01J 49/0463; H01J 49/0445
See application file for complete search history.

(56) References Cited

U.S. PATENT DOCUMENTS

| | | |
|---|---|---|
| 2003/0193020 A1 | 10/2003 | Van Berkel |
| 2004/0128789 A1* | 7/2004 | Harris ...................... A47L 9/02 15/353 |
| 2010/0224013 A1* | 9/2010 | Van Berkel ......... H01J 49/0431 73/863.81 |
| 2012/0083045 A1 | 4/2012 | Van Berkel et al. |
| 2014/0096624 A1* | 4/2014 | ElNaggar ................. G01N 1/14 73/864.34 |

FOREIGN PATENT DOCUMENTS

| | | |
|---|---|---|
| JP | 2002-39927 A1 | 2/2002 |
| JP | 2003-017538 A1 | 1/2003 |
| JP | 2005-523456 A1 | 8/2005 |
| JP | 2008-132401 A1 | 12/2008 |
| JP | 2011-128033 A1 | 6/2011 |
| JP | 2011-232182 A1 | 11/2011 |
| JP | 2012-132826 A1 | 7/2012 |
| JP | 2012-519847 A1 | 8/2012 |
| WO | 2010101656 A1 | 9/2010 |

OTHER PUBLICATIONS

Taylor, Howard E., "Inductively Coupled Plasma-Mass Spectrometry: Practices and Techniques", Elsevier Science & Technology, p. 1-6, Oct. 25, 2000. ProQuest Ebook Central, XP055460269.

* cited by examiner

AUTOMATIC LOCALIZED SUBSTRATE ANALYSIS DEVICE AND ANALYSIS METHOD

CROSS REFERENCE TO RELATED APPLICATION

This application is a U.S. National Phase entry of PCT/SP2015/070681 filed Jul. 21, 2015 which claim priority fro Japanese patent application P2014-167171 filed Aug. 20, 2014.

TECHNICAL FIELD

The present invention relates to an apparatus in which local analysis of a substrate with an inductively coupled plasma mass spectrometry (ICP-MS) apparatus is automated, and an analysis method with the apparatus. The invention also relates to an apparatus capable of performing local analysis with collection of a trace element from a substrate surface and analysis of the collected trace element with ICP-MS, successively and simultaneously.

BACKGROUND ART

A substrate, such as a semiconductor wafer, is manufactured by cutting an ingot formed of, for example, silicon. An unintended impurity element sometimes admixes in a local region of a substrate surface due to, for example, segregation and admixture with a foreign substance when the ingot is manufactured. Accordingly, various analysis apparatuses that perform, for example, entire surface analysis, edge analysis, and local analysis, are used to specify the impurity element included in the acquired substrate and a present position of the impurity element. As examples of an apparatus that performs the entire surface analysis to the substrate, out of these apparatuses, apparatuses including etching means that etches a wafer formed of, for example, silicon, and analysis means that analyzes an impurity element in an etchant, have been known. These apparatuses for entire surface analysis collectively analyze the impurity element included in the entire substrate surface. Thus, when the impurity element is present only at a part of the substrate, such as an edge portion or a local region portion, it is unknown where the impurity element is present on the substrate. When an accurate contamination position of the impurity element has not been ascertained, a position to which the local analysis is performed cannot be determined, and a distribution condition of the impurity element cannot be specified.

Accordingly, as examples of an analysis apparatus that conveniently specifies the distribution condition of the impurity element on the substrate prior to the local analysis, a total reflection X-ray fluorescence spectrometry apparatus, a secondary ion mass spectrometry (SIMS) apparatus, and an apparatus with photoluminescence have been known. For example, a total reflection X-ray fluorescence spectrometry apparatus described in Patent Document 1 can nondestructively, conveniently detect in-plane arrangement of an impurity element.

Here, in substrate analysis of, for example, a semiconductor wafer, a semiconductor device with a substrate is required to improve element performance and yield for mass production of a device miniaturized with high precision. Accordingly, there is a demand for specifying even a contamination source minute in quantity, desirously in terms of the substrate to be a raw material of these devices. Thus, a substrate analysis apparatus is required to have high precision necessary for detecting a local impurity element minute in quantity included in a substrate. However, the total reflection X-ray fluorescence spectrometry apparatus can nondestructively perform convenient analysis, but sometimes fails to detect presence of an impurity element when the abundance of the impurity element included in a substrate is minute in quantity. Additionally, only limited types of impurity elements can be measured. SIMS can perform local analysis, but fails to detect an impurity element minute in quantity similarly to the total reflection X-ray fluorescence spectrometry apparatus. Specifically, the concentration of an impurity element detectable by total reflection X-ray fluorescence spectrometry (TRXRF) is in a range from $10^{10}$ to $10^{12}$ atoms/cm$^2$. The concentration of an impurity element detectable by the SIMS is in a range from $10^9$ to $10^{10}$ atoms/cm$^2$.

An example of an analysis apparatus capable of performing analysis with high precision even when the abundance of an impurity element included on a substrate is minute in quantity, includes an inductively coupled plasma mass spectrometry (ICP-MS) apparatus. ICP-MS can detect, for example, trace contamination at sub-ppt level (pg/mL). Additionally, when a substrate surface includes a plurality of impurity elements, the ICP-MS can further specify the types of the impurity elements and the abundance of each of the elements. As described above, when an impurity element locally included in a substrate surface is analyzed by use of the ICP-MS, for example, analysis in which a protective film adheres to portions except a local region to be analyzed (e.g., refer to Patent Document 2) or apparatuses each that make vapor of etching gas for etching a substrate come in contact (e.g., refer to Patent Documents 3 and 4) can be applied.

In analysis with the ICP-MS, an apparatus that has adopted a nozzle for substrate analysis and collects an impurity element present on a substrate with analysis liquid minute in quantity as much as possible, has been known, as in an apparatus in Patent Document 4. An example of the nozzle for substrate analysis is a nozzle for substrate analysis illustrated in FIG. 5 (e.g., refer to Patent Document 5). In FIG. 5, the nozzle for substrate analysis 500 supplies analysis liquid supplied to an analysis liquid vessel 510, to a substrate W through an analysis-liquid supply pipe 520 so that surface tension can retain analysis liquid D minute in quantity at a centroclinal nozzle end portion 550. Accordingly, retaining the analysis liquid minute in quantity allows a contaminant on the substrate to be collected.

RELATED ART DOCUMENT

Patent Documents

Patent Document 1: JP 2012-132826 A
Patent Document 2: JP 2003-17538 A
Patent Document 3: JP 2002-39927 A
Patent Document 4: JP 2011-232182 A
Patent Document 5: JP 2008-132401 A

SUMMARY OF THE INVENTION

Problems to be Solved by the Invention

However, the above analysis apparatus with ICP-MS temporarily collects the analysis liquid into a collection container, such as a vial, after collecting the analysis liquid including the impurity element. Then, element analysis with ICP-MS is inevitably performed through human hands. In the analysis, there is a risk of influence of external contamination, and additionally loss of time is large due to the manual operation. Therefore, an object of the present invention is to provide an analysis apparatus in which a process is automated from collection of analysis liquid including an impurity element to local analysis with ICP-MS.

Means for Solving the Problems

The present inventors examined an apparatus in which local analysis with an inductively coupled plasma mass spectrometry (ICP-MS) apparatus is automated. In this examination, the automation of an apparatus including a nozzle for substrate analysis was realized. As a result, the present invention has been made. The apparatus including the nozzle for substrate analysis was selected because it was thought that miniaturizing the nozzle allowed sampling from a local region having a further minute area and additionally limiting the quantity of analysis liquid to be ejected allowed analysis of an element further minute in quantity.

The present invention relates to an automatic analysis apparatus for a local region of a substrate, including: a pump that supplies analysis liquid; a nozzle for local analysis that ejects the analysis liquid supplied from the pump onto a predetermined region of a substrate surface to transfer an object to be analyzed in the predetermined region to the analysis liquid, and takes in the analysis liquid to collect the object to be analyzed; a nebulizer that sucks the analysis liquid including the object to be analyzed, in the nozzle for local analysis by negative pressure; an inductively coupled plasma mass spectrometry apparatus that analyzes the object to be analyzed included in the analysis liquid fed from the nebulizer, the nozzle for local analysis including analysis-liquid supply means that ejects the analysis liquid onto the substrate, analysis-liquid discharge means that takes the analysis liquid including the object to be analyzed from the substrate into the nozzle for local analysis to feed the analysis liquid to the nebulizer, and exhaust means including an exhaust channel in the nozzle for local analysis; automatic liquid-feed means that automatically feeds the analysis liquid including the object to be analyzed, taken into the nozzle for local analysis, to the inductively coupled plasma mass spectrometry apparatus; flow adjustment means that adjusts a flow of the analysis liquid to be supplied from the pump to the nozzle for local analysis and a flow of the analysis liquid to be fed from the nozzle for local analysis to the nebulizer; and automatic control means that simultaneously performs the taking-in of the analysis liquid by the nozzle for local analysis and analysis of the object to be analyzed by the inductively coupled plasma mass spectrometry apparatus to perform automatic analysis to a plurality of the adjacent predetermined regions of the substrate, successively.

The automatic analysis apparatus of the present invention has the automatic liquid-feed means that automatically feeds the analysis liquid including the object to be analyzed, taken into the nozzle for local analysis, to the inductively coupled plasma mass spectrometry apparatus. Thus, external contamination is inhibited and the analysis can be promptly performed. There is provided the automatic control means that simultaneously performs both of the taking of the analysis liquid with the nozzle for local analysis and the analysis of the object to be analyzed, by the inductively coupled plasma mass spectrometry apparatus and successively performs the automatic analysis to the plurality of the adjacent predetermined regions. Thus, a distribution condition can be specified for an element present even in minute quantity (e.g., $10^8$ atoms/cm$^2$ or less) only at a specific position on the substrate.

The analysis liquid in the nozzle for local analysis is piped to the nebulizer coupled to ICP-MS to be directly feedable without, for example, a vial, so that the automatic liquid-feed means can be configured. The automatic control means may be made to be individually or collectively, computationally able to control, for example, the supply of the analysis liquid of the pump, the ejecting quantity of the analysis liquid from a leading end portion of the nozzle for local analysis, the sucking quantity of the analysis liquid to the nebulizer, and the feeding quantity to the ICP-MS, or may control the ejecting quantity of the analysis liquid from the leading end portion of the nozzle for local analysis, simultaneously with the analysis speed of the ICP-MS.

Here, when an apparatus that simply adopts only the automatic liquid-feed means, namely, an analysis apparatus capable of directly feeding the analysis liquid of the nozzle for local analysis to the nebulizer without a human-hands medium, such as a vial, is provided in comparison to a conventional analysis apparatus, there is a problem with adjustment of the quantity of the analysis liquid to be ejected from the nozzle for local analysis to a predetermined region to be analyzed. The quantity of the analysis liquid ejected from the nozzle for local analysis with respect to the predetermined region on the substrate, is required to remain constant accurately, to analyze accurately the predetermined region on the substrate. Particularly, the present invention provides the automatic control means to be described later, and allows analysis of a plurality of predetermined regions on a substrate successively. When the local analysis successively continues, the quantity of the analysis liquid to be ejected from the nozzle for local analysis, needs to be kept constant continuously during the analysis. Accordingly, the present invention provides the flow adjustment means that adjusts the flow of the analysis liquid to be supplied from the pump to the nozzle for local analysis and the flow of the analysis liquid to be fed to the nebulizer. The flow adjustment means can conveniently adjust the quantity of the analysis liquid to be supplied to the nozzle for local analysis, with the flow of the pump. On the other hand, negative pressure is used for the feeding to the nebulizer because of a reason to be described later so that the flow adjusting means can adjust the flow by adopting the following structure. Namely, the feeding quantity of the analysis liquid to the nebulizer can be adjusted by any of supplying inert gas to the nebulizer together with the analysis liquid and making the supply of the inert gas adjustable, adjusting the inner diameter and the length of an analysis-liquid supply pipe to be coupled to the nebulizer, and providing the pump for quantity adjustment between the nozzle for local analysis and the nebulizer, or a combination thereof.

Next, the nozzle for local analysis of the present invention will be described. The nozzle for local analysis of the present invention includes: the analysis-liquid supply means that ejects the analysis liquid onto the substrate; the analysis-liquid discharge means that takes the analysis liquid including the object to be analyzed from the substrate into the nozzle for local analysis to feed the analysis liquid to the nebulizer; and the exhaust means including the exhaust channel in the nozzle for local analysis. As described above, the conventional substrate analysis apparatus is assumed to transfer an object to be analyzed on a substrate to the analysis liquid, collect the analysis liquid, temporarily store the analysis liquid in, for example, a vial, and analyze the analysis liquid with the ICP-MS. As illustrated in FIG. 5, the nozzle to be adopted includes one pipe to be used for the supply pipe that ejects the analysis liquid to the substrate and a discharge pipe that takes the ejected analysis liquid into the nozzle. In contrast, the substrate analysis apparatus of the present invention includes separate channels for the analysis-liquid supply means and the analysis-liquid discharge means to perform the taking of the analysis liquid into the nozzle for local analysis and element analysis with the ICP-MS, simultaneously. Specifically, a nozzle for local analysis preferably has two pipes including a supply pipe capable of ejecting the analysis liquid onto the substrate, coupled to the pump, and a discharge pipe that feeds the analysis liquid taken from the substrate to the nozzle, coupled to the nebulizer. The "nozzle for local analysis" is referred to as a "nozzle" below in some cases.

As described above, the conventional nozzle assigns the single pipe to supply the analysis liquid onto the substrate and to take the analysis liquid from the substrate. As the analysis liquid vessel 510 in FIG. 5, a space for storing the analysis liquid is provided in the nozzle and the extruding quantity of the analysis liquid is adjusted so that the quantity of the analysis liquid to be ejected onto the substrate can be conveniently and finely adjusted. In contrast, the present invention provides no vessel for storing the analysis liquid in the nozzle differently from the conventional nozzle so that the quantity of the analysis liquid on the substrate becomes difficult to be finely adjusted. This is because the quantity of the analysis liquid to be ejected onto the substrate and the quantity of the analysis liquid to be taken from the substrate into the nozzle are required to be adjusted by individual flows of the separate channels being the analysis-liquid supply means and the analysis-liquid discharge means. Namely, the present invention provides the separate channels being the analysis-liquid supply means and the analysis-liquid discharge means so that keeping a difference between the ejecting quantity of the analysis liquid from the nozzle onto the substrate and the taking quantity from the substrate into the nozzle, constant, is difficult. Specifically, for example, when a 12-inch wafer is used in a case where an entire surface of the wafer is analyzed, the analysis is performed by sweeping the nozzle for 25 minutes with a nozzle diameter of 10 mm or for 50 minutes with a nozzle diameter of 5 mm. During the period of the analysis, the difference between the ejecting quantity and the taking quantity, is difficult to keep constant continuously. In this manner, the nozzle for local analysis of the present invention easily increases or decreases the quantity of the analysis liquid to be supplied to the substrate in comparison to the conventional nozzle. When the analysis liquid ejected from the nozzle becomes excessive, the analysis liquid sometimes overflows a predetermined region on the substrate and, for example, spreads out to portions other than a portion to which the local analysis is performed.

When a formed film, such as an oxide film or a nitride film, is provided on the substrate, removal of the formed film by, for example, etching is required as a front-end process. When the local analysis is performed to the substrate after the etching, the quantity of the analysis liquid in the nozzle also easily increases. Since $H_2O$ remains on the substrate as a by-product due to the etching, the quantity of the analysis liquid increases as the local analysis continues. When the quantity of the analysis liquid becomes excessive, the analysis liquid sometimes overflows from the nozzle and then spreads out in the same manner above.

Based on the background, the nozzle for local analysis of the present invention includes the exhaust means with the exhaust channel in the nozzle in addition to the analysis-liquid supply means and analysis-liquid discharge means. The local analysis is performed with the nozzle retaining a low pressure atmosphere in the nozzle and exhausting so that the analysis liquid can be retained in the nozzle even when the quantity of the analysis liquid in the nozzle becomes excessive. As a result, the overflow of the analysis liquid can be prevented. Note that, the above flow adjustment means adjusts the flow of the analysis liquid of each of the pump and the ICP-MS to be substantially equivalent so that the substrate analysis apparatus of the present invention can retain the quantity of the analysis liquid on the substrate substantially constant. However, the flow of the analysis liquid to be fed to the nebulizer, to be adjusted by the flow adjustment means is difficult to measure in real time. Typically, the flow is acquired from the weight decreasing quantity of the analysis liquid during a certain period. Accordingly, since, for example, the analysis liquid slightly larger than the calculated feeding quantity to the nebulizer, is often supplied to the nozzle for local analysis when the flow adjustment means is used, the increase or the decrease of the quantity of the analysis liquid still occurs even when the flow adjustment means is provided. Based on the background, the present invention provides the exhaust means in the nozzle in addition to the flow adjustment means, and can completely deal with the increase or the decrease of the quantity of the analysis liquid on the substrate.

Preferably, the nozzle for local analysis of the present invention includes an end portion that supplies the analysis liquid to the substrate, cylindrical in nozzle shape, and includes an internal space capable of retaining the analysis liquid along an internal wall of a cylindrical portion at the cylindrical end portion. Even when a liquid level of the analysis liquid in the nozzle rises in a case where the supply of the analysis liquid into the nozzle has been excessive, the analysis liquid is retained along the internal wall of the cylindrical end portion so that the analysis liquid barely overflows out of the nozzle.

Here, in conventional substrate analysis, making the quantity of the analysis liquid minute in quantity as much as possible so that a contaminant further minute in quantity can be collected, has been technically, commonly known. Accordingly, a nozzle to be adopted in the conventional substrate analysis apparatus typically adopts a nozzle shape that can retain analysis liquid minute in quantity and barely falls off. For example, the nozzle leading end is made to be centroclinal in the conventional nozzle in FIG. 5 so that the surface tension can retain the analysis liquid minute in quantity. In contrast, as described above, the automatic analysis apparatus of the present invention includes the separate channels for the analysis-liquid supply means and the analysis-liquid discharge means. Thus, a problem completely different from that of the conventional nozzle that continuously makes the analysis liquid minute in quantity and constant, occurs in that a case where the supply of the analysis liquid from the nozzle to the substrate becomes excessive, may occur.

Based on the background, the present invention adopts a shape capable of retaining the analysis liquid larger in quantity in the nozzle with respect to the conventional analysis nozzle that has adopted the nozzle shape effective in retaining the analysis liquid minute in quantity. Namely, the conventional analysis nozzle (e.g., a nozzle including a centroclinal leading end similarly to the nozzle leading end 550 in FIG. 5) is suitable for retaining the analysis liquid minute in quantity, but the retainable quantity of the analysis liquid is limited, and the conventional analysis nozzle cannot be applied to the automatic analysis apparatus of the present invention that needs to retain excessive analysis liquid. Meanwhile, in the present invention, the nozzle for local analysis including the nozzle end portion having at least cylindrical shape and the internal space capable of retaining the analysis liquid along the internal wall of the cylindrical portion, can adjust the quantity of the analysis liquid in contact with the substrate surface (a surface area), within a predetermined range, and can also retain the excessive quantity of the analysis liquid, retaining the analysis liquid along the nozzle internal wall even when the quantity of the analysis liquid increases due to excessive supply from the analysis-liquid supply means. As described above, the nozzle for local analysis of the present invention includes the exhaust means so that the nozzle having the above shape can retain the excessive quantity of the analysis liquid along the nozzle internal wall. For example, even when a nozzle having no exhaust means includes a nozzle shape having an internal space capable of retaining the analysis liquid along an internal wall of a cylindrical portion, as described above, the analysis liquid overflows from the nozzle due to empty weight when the analysis liquid to be retained on the nozzle internal wall increases. In this manner, the nozzle having the above shape includes the exhaust means so that the excessive analysis liquid can be retained. The quantity of the analysis liquid retainable in the nozzle for local analysis of the present invention can be controlled by adjusting the length of the nozzle.

In terms of the quantity of analysis liquid to be supplied to a nozzle, the conventional analysis nozzle can supply analysis liquid with a quantity from approximately 200 to 1000 μL into, for example, the analysis liquid vessel in the nozzle, whereas the nozzle for local analysis of the present invention can supply analysis liquid with a quantity from approximately 20 to 100 μL. In this manner in comparison to the conventional analysis nozzle, the nozzle for local analysis of the present invention is miniaturized, and the local analysis with the analysis liquid having a quantity of 100 μL or less allows the element analysis with high precision. On the other hand, the conventional analysis apparatus fails to make the analysis liquid minute in quantity, such as less than 200 μL, when the ICP-MS performs the local analysis. This is because, when the ICP-MS performs measurement, the analysis liquid to be measured is required to be filled in a coupling pipe from a nebulizer to the ICP-MS in addition to the quantity of the analysis liquid to be introduced to the ICP-MS during time necessary for the measurement (approximately 3 minutes depending on the number of elements to be measured). In a case where, for example, the nebulizer performs negative pressure suction during the ICP-MS analysis, when the analysis liquid in the coupling pipe disappears, resistance decreases and then the flow unintendedly increases. Thus, the sensitivity of the ICP-MS considerably varies so that the analysis cannot be accurately performed. Accordingly, the conventional analysis apparatus requires the analysis liquid having at least a quantity of 200 μL or more. In contrast, in the present invention, the plurality of the adjacent predetermined regions is successively analyzed. Even when the quantity of the analysis liquid is arranged to be 200 μL or less for one region, the analysis liquid for analyzing adjacent another region is successively supplied to the ICP-MS so that any of the analysis liquid can be continuously filled in the pipe between the nebulizer and the ICP-MS. Accordingly, the present invention can reduce the analysis liquid to be used for the local analysis per region, by half or less, and can perform the element analysis with high precision.

As examples of the pump that supplies the analysis liquid to the nozzle for local analysis described above, a positive displacement pump, such as a piston pump, a plunger pump, or a syringe pump, is preferably adopted and the syringe pump is more preferable. This is because the supply of the analysis liquid can be relatively, accurately retained.

The substrate analysis apparatus of the present invention includes the analysis liquid collected with the above nozzle for local analysis, arranged feedable to the nebulizer by negative pressure suction. For example, negative pressure occurs due to supply of inert gas, such as Ar, to the nebulizer so that the analysis liquid can be fed to the nebulizer by the negative pressure. Specifically, when the inert gas is supplied to the nebulizer by 1 L per minute, the negative pressure can feed the analysis liquid having a quantity from approximately 20 to 100 μL per minute, to the nebulizer. Here, the negative pressure suction is adopted as the analysis liquid supply means because a so-called "memory" in which the analysis liquid remains at a dead volume portion in the pump and a target object to be subsequently measured is contaminated, barely occurs. The analysis apparatus of the present invention successively performs the automatic analysis to the plurality of the adjacent predetermined regions on the substrate. When the memory occurs in a supply channel between the nozzle for local analysis and the nebulizer, analysis results with respect to the predetermined regions on the substrate become inaccurate. Thus, a difference easily occurs in simultaneous analysis including both of the local analysis by the nozzle and the analysis of the object to be analyzed by the ICP-MS. Accordingly, when a pump is provided as the flow adjustment means, a pump that makes the remainder small to the dead volume, is preferably adopted. For example, a peristaltic pump can be adopted. However, although the remainder of the dead volume is small when the peristaltic pump is used, consideration for contamination from a tube included in the pump is required because the present invention has a purpose of trace element analysis. Note that, a conventionally, publicly known implement can be adopted as the nebulizer. A conventionally known apparatus can also be adopted to the inductively coupled plasma mass spectrometry apparatus.

As examples of the substrate to be analyzed by the above automatic analysis apparatus, various substrates, such as semiconductor wafers and glass substrates, can be objects to be analyzed, and the semiconductor wafers are preferable. For the plurality of the adjacent predetermined regions to which the local analysis is performed, only a contamination region in which presence of an impurity element has been specified by to some extent, for example, a total reflection X-ray fluorescence spectrometry method, may be analyzed, or the local analysis may be successively performed to the entire substrate. Note that, when a substrate having a hydrophilic formed film, such as an oxide film or a nitride film, on the substrate, is analyzed, the formed film is preferably, previously etched and removed. This is because the analysis liquid ejected from the nozzle is prevented from spreading out on the hydrophilic film.

As a method of performing automatic analysis to a local region of a substrate surface by use of the above analysis apparatus, the following automatic analysis method for a local region of a substrate can be applied, the method including the steps of: performing local analysis of collecting an object to be analyzed included in a predetermined region on a substrate into the nozzle for local analysis by taking analysis liquid including the object to be analyzed from the substrate into the nozzle for local analysis by the analysis-liquid discharge means after the analysis-liquid supply means of the nozzle for local analysis ejects the analysis liquid supplied from the pump into the nozzle for local analysis, onto the predetermined region of a substrate surface; and performing analysis of the object to be analyzed of performing the automatic analysis to the object to be analyzed included in the analysis liquid by sucking the analysis liquid including the object to be analyzed from an inside of the nozzle for local analysis to the nebulizer by the negative pressure and by feeding the analysis liquid to the inductively coupled plasma mass spectrometry apparatus. The step of performing the local analysis is performed with the exhaust means exhausting the inside of the nozzle for local analysis, and the flow adjustment means makes a flow of the analysis liquid to be supplied from the pump to the nozzle for local analysis equivalent to or more than a flow of the analysis liquid to be fed from the nozzle for local analysis to the nebulizer.

As described in detail in the invention relating to the analysis apparatus, in the present invention in which the analysis liquid collected by the nozzle for local analysis is automatically fed to the ICP-MS, the quantity of the analysis liquid to be ejected from the nozzle is required to remain constant continuously during the continuation of the successive local analysis of the substrate. Particularly, since the analysis liquid collected with the nozzle for local analysis is sucked into the nebulizer by the negative pressure, the quantity of the analysis liquid in the nozzle is difficult to be accurately and finely adjusted. Accordingly, when the quantity of the analysis liquid in the nozzle for local analysis becomes excessive, the analysis liquid ejected from the nozzle may overflow out of the predetermined regions. Conversely, when the quantity of the analysis liquid in the nozzle for local analysis decreases, the quantity of the analysis liquid to be ejected becomes insufficient. When the quantity of the analysis liquid is excessively insufficient, the nebulizer sucks air around the analysis liquid so that accurate analysis gets into difficulty.

Based on the background, the analysis method of the present invention performs the step of the local analysis with the exhaust means exhausting the inside of the nozzle for local analysis, and additionally the quantity of the analysis liquid to be fed from the pump to the nozzle is made to be equivalent to or more than the quantity of the analysis liquid to be fed from the nozzle to the nebulizer. The local analysis is performed with the exhaust means exhausting so that the analysis liquid can be prevented from overflowing from the nozzle even when the quantity of the analysis liquid in the nozzle for local analysis becomes excessive. During the exhaust by the exhaust means, certain external air is introduced between the analysis liquid on the substrate, ejected from the nozzle for local analysis, and a nozzle end portion. Thus, the analysis liquid is arranged on a spherical surface, along the nozzle end portion so that the overflow out of the nozzle is prevented. Additionally, the flow adjustment means makes the flow of the analysis liquid to be supplied from the pump to the nozzle equivalent to or more than the analysis flow of the ICP-MS so that the quantity of the analysis liquid in the nozzle can be prevented from being insufficient.

Advantageous Effects of the Invention

As described above, in the present invention, the analysis can be automated for a trace element included in a predetermined region on a substrate, and additionally a plurality of the adjacent predetermined regions can be successively analyzed. Accordingly, analysis precision can be improved by reducing the quantity of analysis liquid in comparison with the conventional case, and a present position of the trace element on the substrate can be specified.

DESCRIPTION OF EMBODIMENTS

An embodiment of the present invention will be described below.

Figure 1:
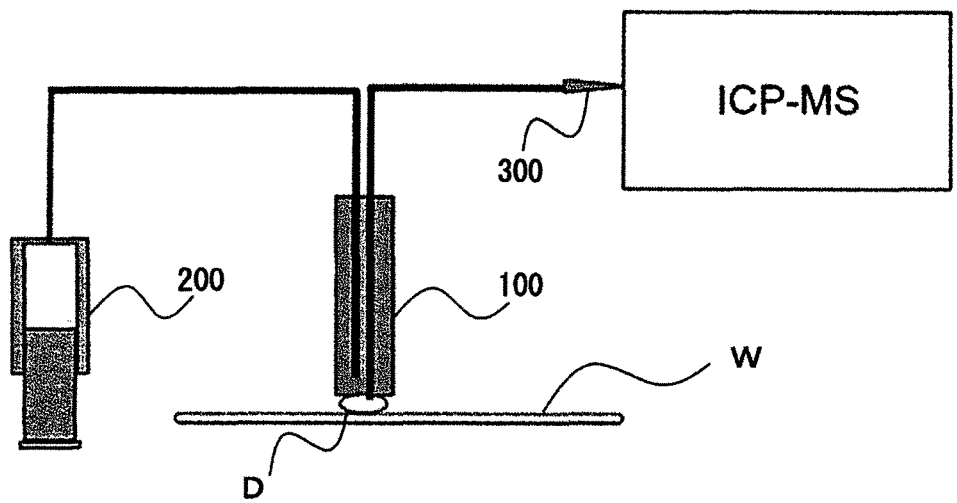
FIG. 1 is a schematic sectional view of an automatic analysis apparatus in an embodiment.

In the present embodiment, local analysis of a substrate was performed by use of an automatic analysis apparatus illustrated in FIG. 1. A nozzle for local analysis 100 is coupled to a syringe pump 200, and analysis liquid can be fed into the nozzle 100 by the syringe pump 200. The analysis liquid in the nozzle 100 is fed to a nebulizer 300 to be automatically feedable to ICP-MS. Note that, an inert gas supply channel capable of supplying Ar gas is coupled to the nebulizer 300, separately from a discharge tube (not illustrated).

Figure 2:
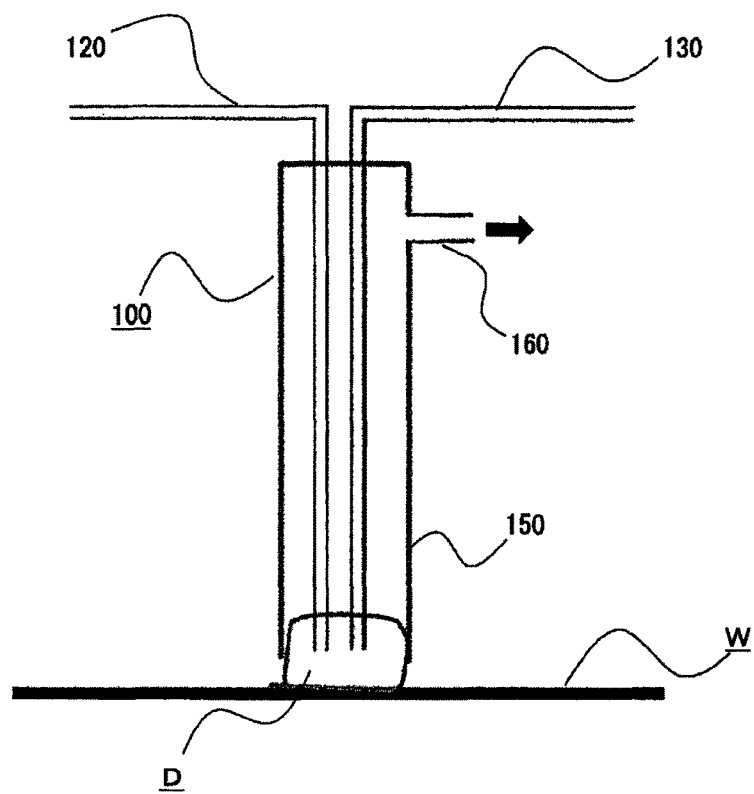
FIG. 2 is a sectional view of a nozzle for local analysis in the embodiment.

FIG. 2 is a sectional view of the nozzle for local analysis 100. As illustrated in FIG. 2, the nozzle for local analysis 100 includes a substantially cylindrical nozzle body, a supply tube 120 coupled to the syringe pump 200, and the discharge tube 130 coupled to the nebulizer 300. The supply tube 120 supplies the analysis liquid from the syringe pump 200 into the nozzle 100 so that the analysis liquid can be ejected onto a substrate W. The discharge tube 130 collects analysis liquid D from the substrate W so that the analysis liquid D can be fed to the nebulizer 300. Exhaust means 160 capable of exhausting in a direction of an arrow is provided inside the nozzle for local analysis 100, and is coupled to an exhaust pump (not illustrated).

Figure 3:
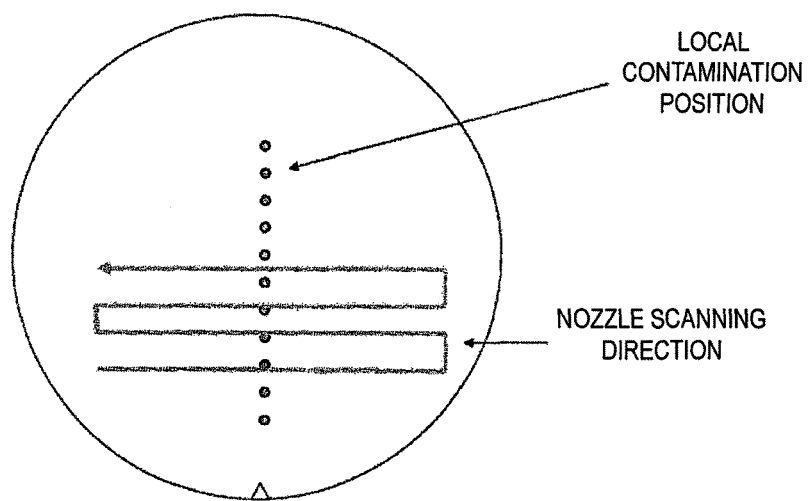
FIG. 3 is a view illustrating a local contamination condition and nozzle operation during analysis in the embodiment.

A specific analysis method by the use of the analysis apparatus will be described. A wafer substrate including a 12-inch silicon was used as a substrate to be analyzed. Contamination solution including Sr, Ba, Cd, Li, Mo, and Pb, each element having a quantity of 10 ppb(ng/mL) mixed, was locally dropped every 5 μL onto the wafer substrate as illustrated in FIG. 3 so that a locally contaminated substrate was prepared.

Figure 4:
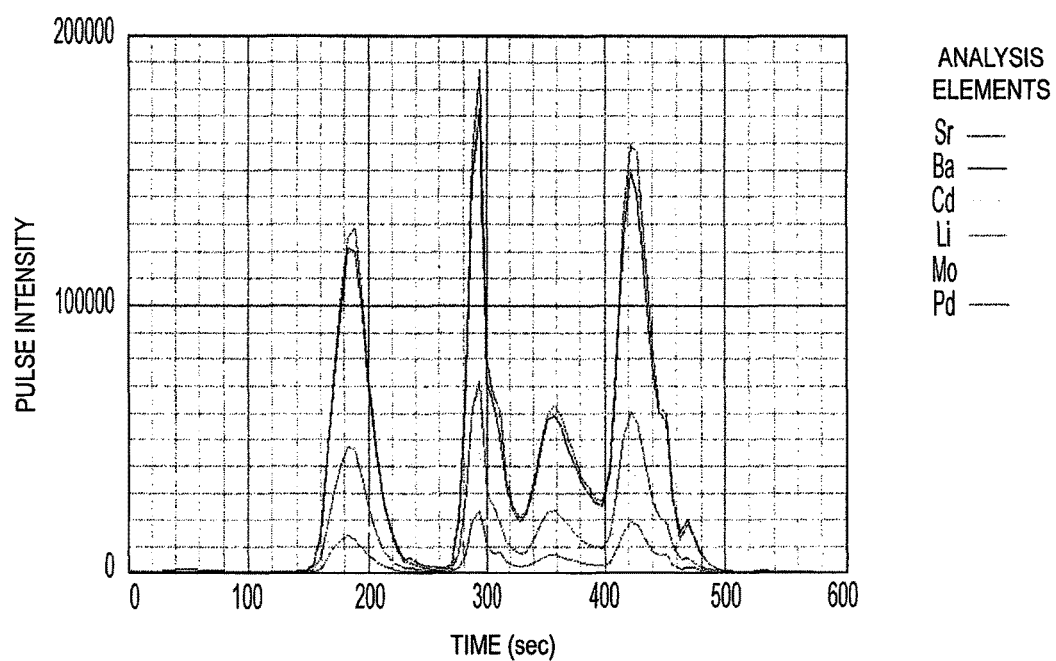
FIG. 4 is a graphical representation of an ICP-MS analysis result in the embodiment.
Figure 5:
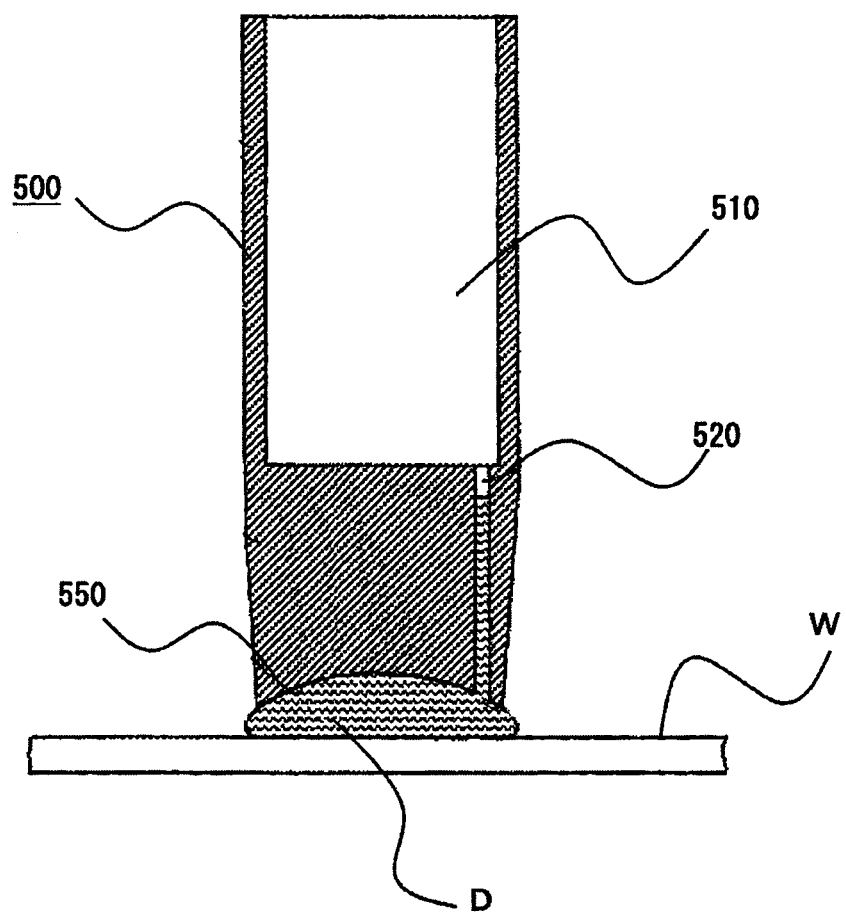
FIG. 5 is a schematic view of a conventional nozzle for substrate analysis.

The local analysis was performed to the contaminated substrate by the use of the analysis apparatus illustrated in FIG. 1. First, the analysis liquid including 3% HF and 4% $H_2O_2$, in a quantity of 1500 μL was filled in a PFA tube coupled between the syringe pump and the nozzle. Then, the analysis liquid was supplied to the nozzle by the syringe pump, and the analysis liquid in a quantity of 100 μL was ejected on the substrate through the supply tube. In this case, the exhaust pump exhausted at an exhaust speed from 0.3 to 1.0 L/min in the direction of the arrow in FIG. 2. Accordingly, after the objects to be analyzed present on a substrate surface were transferred into the analysis liquid, the analysis liquid D was sucked and taken into the nozzle through the discharge tube. Then, the Ar gas in a quantity of 1.0 L per minute was supplied to the nebulizer through the inert gas supply channel so that negative pressure occurred. The analysis liquid including the objects to be analyzed in the nozzle, was fed to the nebulizer at a flow of approximately 100 μL/min. Next, analysis was performed by the ICP-MS. In the analysis, while the nozzle is moved at 10 mm/sec on the substrate to draw a line illustrated by the arrow in FIG. 3, the analysis liquid is ejected and sucked so that the local analysis was successively performed. The element analysis by the ICP-MS was performed to the analysis liquid fed from the inside of the nozzle to the nebulizer, simultaneously with taking of the analysis liquid into the nozzle. The analysis liquid equivalent to or more than the feeding to the nebulizer was supplied to the nozzle by the syringe pump, and was ejected onto the substrate so that the quantity of the analysis liquid on the substrate remained in a quantity of approximately 100 μL. FIG. 4 illustrates an analysis result of the ICP-MS.

As illustrated in FIG. 4, strong intensity peaks of the respective analysis elements were detected at analysis times of approximately 190, 290, 360, and 420 seconds. Checking the moving speed and moving position of the nozzle with detecting times of the element peaks, revealed that the element peaks were detected at analysis times corresponding to the positions at which the contamination solution dropped. Accordingly, the analysis apparatus could ascertain that the contamination positions of the respective analysis elements could be specified.

An analyzing limit with respect to the respective elements based on the analysis result in the present embodiment above, was compared to an analysis limit analyzed by a conventional nondestructive analysis apparatus. In the present embodiment, the substrate enforcedly contaminated by dropping 5 μL including the respective metal elements each in a quantity of 10 ppb(ng/mL), was analyzed. The number of metal atoms of, for example, Fe included in the solution is approximately 5E+11 atoms. Here, the detecting limit of a total reflection X-ray fluorescence apparatus is approximately 1E+11 atoms/cm$^2$ and the area of a measuring portion is 1 cm$^2$, resulting in being substantially the same as the enforcedly contaminated contamination liquid in a quantity of 5 μL (one spot). Thus, the Fe atoms are difficult to be detected from the analysis substrate in the present embodiment. In contrast, in the present embodiment, as illustrated in the result of the ICP-MS in FIG. 4, the Fe atoms can be detected and the detecting limit calculated based on pulse intensity measured by the ICP-MS, is approximately 5E+6 atoms in a spot of 5 μL. The diameter of the nozzle is reduced and a contact area with the wafer is further reduced in size so that an element further minute in quantity can be detected. In this manner, the result in the present embodiment showed that detection sensitivity was higher than the case where the total reflection X-ray fluorescence apparatus was used, and the detection sensitivity for, for example, Fe was higher by approximately 4 digits.

INDUSTRIAL APPLICABILITY

In the present invention, local analysis with ICP-MS can be automated and additionally the automatic analysis can be successively performed to a plurality of adjacent predetermined regions. Accordingly, even for an impurity element minute in contamination quantity on a substrate surface, a present position and the type of the element can be specified. Specifically, in the present invention, an element in a quantity from $10^5$ to $10^7$ atoms/cm$^2$ can be analyzed. Additionally, the quantity of analysis liquid is reduced less than a conventional case, and element analysis with high precision can be achieved.

REFERENCE SINGS LIST 100 nozzle for local analysis
120 analysis-liquid supply means
130 analysis-liquid discharge means
150 nozzle leading end
160 exhaust means
200 pump
300 nebulizer
D analysis liquid
W substrate

The invention claimed is:

1. An automatic analysis apparatus for a local region of a substrate, comprising:
   a pump that supplies analysis liquid;
   a nozzle for local analysis that ejects the analysis liquid supplied from the pump onto a predetermined region of a substrate surface to transfer an object to be analyzed in the predetermined region to the analysis liquid, and takes in the analysis liquid to collect the object to be analyzed;
   a nebulizer that sucks the analysis liquid, including the object to be analyzed, into the nozzle for local analysis by negative pressure;
   an inductively coupled plasma mass spectrometry apparatus, which apparatus analyzes the object to be analyzed, and which object is included in the analysis liquid fed from the nebulizer;
   wherein the nozzle for local analysis is cylindrical in shape and includes a cylindrical end portion that supplies the analysis liquid to the substrate, and which nozzle includes an internal space capable of retaining the analysis liquid along an internal wall of the nozzle at the cylindrical end portion, said nozzle for local analysis further having: an analysis-liquid supply pipe that ejects the analysis liquid onto the substrate; an analysis-liquid discharge pipe that takes the analysis liquid including the object to be analyzed from the substrate into the nozzle for local analysis to feed the analysis liquid to the nebulizer; and an exhaust including an exhaust channel in the nozzle for local analysis,
   an automatic liquid-feed pipe that automatically feeds the analysis liquid including the object to be analyzed, taken into the nozzle for local analysis, to the inductively coupled plasma mass spectrometry apparatus;
   a flow adjustment means that adjusts a flow of the analysis liquid to be supplied from the pump to the nozzle for local analysis and a flow of the analysis liquid to be fed from the nozzle for local analysis to the nebulizer, wherein the flow adjustment means supplies inert gas to an inert gas supply channel connected to the nebulizer to generate a negative pressure, and wherein the flow adjustment means adjusts a quantity of the supply of the inert gas when the analysis liquid is sucked into the nebulizer; and
   an automatic controller that simultaneously performs the taking-in of the analysis liquid with the nozzle for local analysis, and analysis of the object to be analyzed with the inductively coupled plasma mass spectrometry apparatus to perform automatic analysis to a plurality of the adjacent predetermined regions of the substrate, successively, by allowing the flow adjustment means to make a flow of the analysis liquid to be supplied from the pump to the nozzle for local analysis equivalent to or more than a flow of the analysis liquid to be fed from the nozzle for local analysis to the nebulizer wherein the exhaust is configured to maintain a low pressure atmosphere in the nozzle to deal with the increase or the decrease of the flow of the analysis liquid on the substrate.

2. An automatic analysis method for a local region of a substrate surface by use of the apparatus defined in claim 1, comprising the steps of:

performing local analysis by allowing the analysis-liquid supply pipe of the nozzle for local analysis to eject the analysis liquid, supplied from the pump into the nozzle for local analysis, onto the predetermined region of a substrate surface, then taking analysis liquid including the object to be analyzed from the substrate into the nozzle for local analysis by the analysis-liquid discharge pipe, and collecting an object to be analyzed included in a predetermined region on a substrate into the nozzle for local analysis; and performing analysis of the object to be analyzed by sucking the analysis liquid including the object to be analyzed from an inside of the nozzle for local analysis to the nebulizer by the negative pressure which was generated by supplying an inert gas to the inert gas supply channel connected to the nebulizer, then feeding the analysis liquid to the inductively coupled plasma mass spectrometry apparatus, and subjecting the object to be analyzed included in the analysis liquid to the automatic analysis, wherein the step of performing the local analysis is performed with the exhaust exhausting the inside of the nozzle for local analysis, and the flow adjustment means makes a flow of the analysis liquid to be supplied from the pump to the nozzle for local analysis equivalent to or more than a flow of the analysis liquid to be fed from the nozzle for local analysis to the nebulizer.

* * * * *